United States Patent
Ladebeck (10) Patent No.: US 8,717,018 B2
(45) Date of Patent: May 6, 2014

(54) PATIENT POSITIONING COUCH AND COMBINED MEDICAL EXAMINATION DEVICE WITH A PATIENT POSITIONING COUCH

(75) Inventor: Ralf Ladebeck, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 636 days.

(21) Appl. No.: 12/892,318

(22) Filed: Sep. 28, 2010

(65) Prior Publication Data

US 2011/0074407 A1  Mar. 31, 2011

(30) Foreign Application Priority Data

Sep. 29, 2009 (DE) .......................... 10 2009 043 449

(51) Int. Cl.
*G01R 33/00* (2006.01)
*G01R 33/02* (2006.01)
*A61B 6/04* (2006.01)

(52) U.S. Cl.
USPC ............................ 324/261; 324/244; 378/209

(58) Field of Classification Search
USPC .......................................... 378/209; 324/261
See application file for complete search history.

(56) References Cited

U.S. PATENT DOCUMENTS

| | | | | |
|---|---|---|---|---|
| 4,823,774 A | * | 4/1989 | Grasser | 601/4 |
| 6,499,156 B1 | * | 12/2002 | Dirst | 5/81.1 C |
| 6,668,403 B2 | * | 12/2003 | Seufert | 5/601 |
| 2002/0112288 A1 | | 8/2002 | Seufert | |
| 2004/0057557 A1 | * | 3/2004 | Nafstadius | 378/209 |
| 2004/0143177 A1 | | 7/2004 | Falbo | |
| 2007/0050908 A1 | | 3/2007 | Kogan et al. | |

FOREIGN PATENT DOCUMENTS

DE 10108635 A1 9/2002

* cited by examiner

*Primary Examiner* — Bot Ledynh
(74) *Attorney, Agent, or Firm* — Harness, Dickey & Pierce, P.L.C.

(57) ABSTRACT

A patient positioning couch for a combined medical examination device is disclosed. In at least one embodiment, at least one opening is provided in a support plate of the patient positioning couch and the patient positioning couch includes at least one conveyor belt in order to move a patient on the support plate in the longitudinal direction.

20 Claims, 7 Drawing Sheets

PATENT POSITIONING COUCH AND COMBINED MEDICAL EXAMINATION DEVICE WITH A PATIENT POSITIONING COUCH

PRIORITY STATEMENT

The present application hereby claims priority under 35 U.S.C. §119 on German patent application number DE 10 2009 043 449.6 filed Sep. 29, 2009, the entire contents of which are hereby incorporated herein by reference.

BACKGROUND

Different conclusions can be drawn from the image data of various, known medical examination devices. Whilst X-ray based image data provide statements of the attenuation coefficients of the displayed object under examination, knowledge of the proton density or density of the respective, excited nuclei, relaxation parameters and other variables, can be obtained by means of magnetic resonance tomography. On the other hand, positron emission tomography (PET) enables functional imaging to be achieved without the resolution of magnetic resonance tomography, for example.

There is therefore a need for combined medical examination devices which ultimately permit the recording of image data of a plurality of examination devices, in order to achieve amalgamated image data. In particular, better data can then be derived for the diagnosis from this amalgamated image data than if only singular image data are examined, that is to say image data from a single examination device.

At the same time it is desirable to construct the examination devices so as to be spatially uniform in each case. Different examinations, for example magnetic resonance examinations and PET examinations can then be carried out on the patient simultaneously and therefore with a time saving. On the other hand, the recording of image data is extremely simple with this configuration of combined medical examination devices since, due to the simultaneity of the recordings, no movements of the patient have to be corrected and therefore a single calibration of the examination devices together before initial start-up makes subsequent amalgamation of the image data perfectly possible.

A problem of such types of combined devices is in the arrangement of the individual elements. In particular, devices inside the detection units must meet different and partially conflicting requirements for the respective examination devices. For example, to be suitable for magnetic resonance devices, patient positioning couches must not contain any ferromagnetic elements. There is no such requirement for positron emission tomography devices, but in this case the material must attenuate radiation only to a small extent.

It is therefore known for patient positioning couches for combined medical examination devices to be designed in such a way that, in the context of material research, a material is selected that best meets the requirements of the respective medical examination devices.

SUMMARY

In at least one embodiment of the present application, a patient positioning couch is disclosed, which permits use in any combined medical examination devices, along with greater freedom in the choice of material.

In at least one embodiment of the invention, provision is made in the case of a patient positioning couch, for at least one opening to be provided in the support plate of the patient positioning couch and for the patient positioning couch to have at least one conveyor belt in order to move a patient on the support plate in the longitudinal direction.

Naturally this opening is arranged or is intended to be arranged in the region of the detector arrangement of one of the plurality of medical examination devices, so that ultimately for this detector arrangement the patient positioning couch is invisible. Where a magnetic resonance device is combined with a positron emission tomography device, the opening, which is made sufficiently large, is positioned so that it is placed inside the PET detector arrangement during the data recording of the PET detector arrangement—normally a PET detector ring. In this case the material of the patient positioning couch can be chosen independently of the presence of the positron emission tomography device. The inventive construction thus allows a cost reduction in material research since the material to be selected has to be optimized only for one examination device. Recourse can therefore be made to materials that are already known and which were simply not suitable for combined examination devices.

Here the conveyor belt also allows the patient to be moved inside the combined medical examination device in relation to the opening. In the case of a large number of examinations it is necessary to examine large areas of the patient or in extreme cases even the whole body. For this, the patient was previously moved through the PET detector arrangement lying down on the patient positioning couch. A similar arrangement applies to magnetic resonance devices, it being possible in this case of course for the detector arrangements in the form of coils to be placed on the patient prior to the measurement and moved along with the patient through the magnetic resonance device. But to reduce costs, modern magnetic resonance devices have only narrow regions of approximately 30 cm in which the main magnetic field is homogeneous. This expansion is related to the longitudinal direction of the magnetic resonance device, where a homogeneous cylinder is therefore located in the center. Since meaningful imaging is also only possible in this region, correspondingly, in magnetic resonance recordings in order to record overview images the patient is also moved through the homogeneous region of the magnetic resonance device. Since in the inventive arrangement the supporting elements of the patient positioning couch are stationary during data recording, correspondingly the conveyor belt is necessary to facilitate patient movement.

In this case the opening is a cut-out in the material or a break-through in the patient positioning couch; it is so to speak a hole in the patient positioning couch. This is advantageous for all radiation-based examination devices since the radiation to be detected is not therefore attenuated by the patient positioning couch itself.

The opening can preferably divide the patient positioning couch into two large-area plate sections in a partial area of the cross-section. In this case the plate sections are preferably joined at the sides by narrow cross struts. Correspondingly, in this region of the patient positioning couch radiation is indeed attenuated en route to the detector surface; on the other hand patient positioning couches can be produced and installed in the usual manner for magnetic resonance devices for example. Matching to an additional radiation-based detection device is simply achieved by providing an opening in the patient positioning couch and installing a conveyor belt.

Alternately, the opening can divide the patient positioning couch into two separate large-area plate sections over the entire cross-section. In this case, with a particular advantage, at least one plate section is lowerable and/or is moveable in the longitudinal direction of the patient positioning couch and/or partially shaped obliquely to the horizontal. By completely separating the patient positioning couch into two large-area plate sections this creates more freedom in the use of the patient positioning couch. In this case a part of the patient positioning couch can be withdrawn from the combined medical examination device in the usual manner in order to arrange the patient thereon. This plate section can be made longer in the horizontal direction than the two or more existing plate sections. After receiving the patient, the plate section is then raised and moved into the combined medical examination device until the end position is reached. In the end position the opening to be provided according to the invention lies between this plate section supporting the patient and the at least one further plate section. In order to move the patient over the opening, a conveyor belt is to be provided at least at the plate section which carries the patient.

The opening need not be especially wide; a clearance of 20 cm is completely adequate for recording image data with radiation-based detection devices. Nevertheless, the head can be slightly sunk into the opening for example, whereby with further movement the head can be pushed against the following plate section. In order to avoid this, an intermediate element can be provided on the upper side of the patient positioning couch for at least partial covering of the opening. Here the configuration of the intermediate element complies with the configuration of the opening. If the opening simply includes a partial area of the cross-section of the patient positioning couch, that is to say cross struts are provided, the intermediate element can rest on these cross struts, for example. At best, support of the intermediate element is additionally possible on one plate section, provided the latter has no conveyor belt.

In order to avoid such fixing problems, one supporting element for receiving a patient can be provided and this is arranged on at least one conveyor belt. In the simplest case the supporting element can be constructed as a type of plate on which the patient is laid. A type of plastic foam or porous fabric, for example, can be considered for the material. Basically, the material must have such inherent strength that it prevents sinking of any parts of the patient's body into the opening, it additionally being possible for the radiation attenuation to be as low as possible.

In order to keep frictional resistances as low as possible, provision can be made for all plate sections to have their own conveyor belts. In this embodiment, friction can occur only in the area of the opening if an intermediate element is arranged at that point. Otherwise, the conveyor belts of the plate sections are driven so that they facilitate uniform movement of the patient.

Alternately, all plate sections can have a shared conveyor belt. With a particular advantage, the part of the conveyor belt which runs under the support plate can be set at a distance from the support plate so that a space is created between the support plate and the conveyor belt to house items, in particular detector devices. In this embodiment the patient can be transported over the plate sections, it being possible for the conveyor belt itself to cover the opening or openings. If the conveyor belt has sufficient strength in the area of the openings the use of an intermediate element or supporting element can in fact be dispensed with. Furthermore, in order to make the conveyor belt uniform, the use of an intermediate element or a supporting element is of course possible in order to prevent the patient sinking into the opening.

With particular advantage, the conveyor belt can have two belt sections, it being possible for the first section which is used to receive the patient, to have a smooth underside and the second area to have a textured underside. As already described, in the area of the opening the existing material should have as low a radiation attenuation as possible. On the other hand, the conveyor belt must have a certain structure on the underside, at least at points in order to facilitate coupling of the conveyor belt to drive devices. So that these structures do not have a negative influence on the imaging, subdivision of the conveyor belt into at least two sections is therefore necessary. In the first section which lies within possible detection devices and on which the patient is laid, a smooth under surface shall be provided in order to avoid false measurements with the examination device. Due to the separation of the conveyor belt from the support plate, the support plate can provide a second area which lies completely outside possible detector arrangements and which permits any texturing of the underside. Due to this texturing, the conveyor belt can then be coupled to appropriate rollers which facilitate the operation of the conveyor belt.

Advantageously, the conveyor belt can consist of aramid textile fiber. Aramid fiber fabric is also known for use in magnetic resonance devices as well as optimized in radiation-based devices and therefore suitable for use in all possible combined medical examination devices.

In addition, at least one embodiment of the invention also relates to a combined medical examination device having at least two imaging arrangements and one patient positioning couch, it being possible for the patient positioning couch to have at least one opening in the support surface.

Firstly, in the simplest embodiment, the patient positioning couch of the combined medical examination device does not have a conveyor belt. Of course with this patient positioning couch only examinations in special areas, for example cardiac examinations, are possible. For adaptation to examinations of the back, provision can be made for the patient positioning couch to have an opening which lies in the longitudinal direction of the patient positioning couch.

In a development, the combined medical examination device has a patient positioning couch of the type previously described, with opening and conveyor belt.

In the case of a combination of a plurality of imaging arrangements, combined medical examination devices usually consist of two imaging arrangements, it being possible for the first examination device to be an X-ray device or a computer tomography device or a magnetic resonance device. The second examination device can be a positron emission tomography device or a scintigraphy device, in particular a single-photon emission tomography device. Single-photon emission tomography devices are also abbreviated to SPECT which originates from the English designation. Basically, in this connection the combination of all first examination devices with all second examination devices is possible. A preference for the combination of magnetic resonance device and positron emission tomography simply results from the fact that the radiation exposure of the patient is not increased by way of magnetic resonance tomography, which is naturally the case with positron emission tomography. Due to this combination the high resolution of images recorded by way of magnetic resonance tomography can be linked to the functional information from the positron emission tomography images. These advantages do not stand in the way of a combination of a computer tomography device and a positron emission tomography device for example; it is merely a possible variant.

The additional problem arising from the use of a magnetic resonance device as the first examination device is that usually the coils for data recording, that is to say the local coils, are attached to the patient prior to the data recording and moved with the patient through the magnetic resonance device. In this case the local coils are arranged in a coil array. In the course of this different components of the local coils are situated at different locations in the detection field of the second examination device, in particular of a positron emission tomography device. At the same time, the local coils have radiation-attenuating components which interfere with the imaging of the radiation-based detection devices. Preferably, provision can therefore be made for the combined medical examination device to have a stationary coil array in the longitudinal direction of the magnetic resonance device. As a result, the coil array is likewise stationary in relation to the detector device of the second examination device, which is why it can be optimized in relation to these detector devices.

Nevertheless, the coil array should allow matching to the object under examination, in particular to patients of different size and girth. Preferably the geometry of the coil arrays, in particular the diameter, can therefore be variable and/or the coil array can be hinged. Since the coil array is stationary, its linear expansion is limited, irrespective of the definite configuration since the homogeneous region of the constant magnetic field of the magnetic resonance device is likewise limited to the central region. The coil array is obviously positioned in the homogeneous region. Adaptation to different patients is therefore only required in relation to the diameter, it being possible for the adaptation to be ensured by variability of the diameter or tiltability of the coil array.

With particular advantage, in order to arrange the coil array on the patient, at least one section of the coils of the coil array can be attached to a device whose volume can be varied hydraulically or pneumatically. The circumference of this device can thus be varied by supplying or removing air or any gas or liquid. At the same time, the device can be subdivided into chambers in order to adjust the change in volume with maximum pin-point accuracy. The material of the device may be expandable only up to a predetermined volume until the device has assumed a predefined shape.

Alternately, in order to arrange the coil array on the patient, provision can be made for at least one section of the coils of the coil array to be arranged so as to be moveable together on a segmented structure. In this case, one or a plurality of coils is attached to an individual segment. The coils are then moved to the desired position by the displacement of the segments. The displaceability of the segments can be realized by retainers at the edge of the segments.

In both cases, as well as the use of a variable-volume device and the use of a segmented structure, the coils above and at the side of the patient shall be arranged to be variable. The coils beneath the patient can be fixed for example in an arrangement in an intermediate element covering the opening.

With particular advantage, the coil array can be formed in a central region in relation to the longitudinal axis, with less radiation attenuation than in the peripheral regions. As already described, radiation attenuation is only relevant in the region of any detector device. The detection region of the magnetic resonance device usefully overlaps the detection region of the positron emission tomography device to allow simultaneous recording of an identical volume of the object under examination. In order to prevent interference with the PET detector arrangement, it is therefore possible to keep the radiation-attenuating parts of the coil array away from the detection range of radiation-based detection devices, for example a positron emission tomography device.

BRIEF DESCRIPTION OF THE DRAWINGS

Further advantages, features and details of the invention are disclosed in the example embodiments described below, as well as with the aid of the drawings, where.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
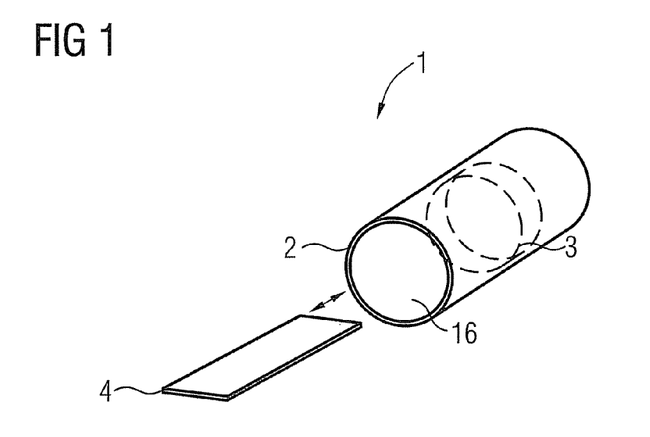
FIG. 1 shows a schematic representation of an inventive combined medical examination device.

FIG. 1 shows a purely schematic representation of a combined medical examination device 1, including a magnetic resonance device 2 and a positron emission tomography device 3. The magnetic resonance device 2 is provided with a cylindrical bore 16, in which the patient is placed on the patient positioning couch 4 for measurements and examinations to be carried out. In this connection it is known that space-saving constructions can be realized in such a way that the body coil of the magnetic resonance device 2 and the detector device of the positron emission tomography device 3 are manufactured and installed as a single device. For this, the detector elements of the positron emission tomography device 3 are either built into the circuit-board conductors of the body coil of the magnetic resonance device 2 or the circuit-board conductors of the body coil are passed through between the detector elements of the positron emission tomography device 3. For the sake of clarity, other known components of the combined medical examination device 1 in FIG. 1 have not been shown. For example, it is obvious that the magnetic resonance device 2 and the positron emission tomography device 3 are controlled by a control device. Here the control device can advantageously control both the magnetic resonance device 2 and the positron emission tomography device 3 or the patient positioning couch 4. Obviously the magnetic resonance device 2 has gradient coils for imaging.

Figure 2:
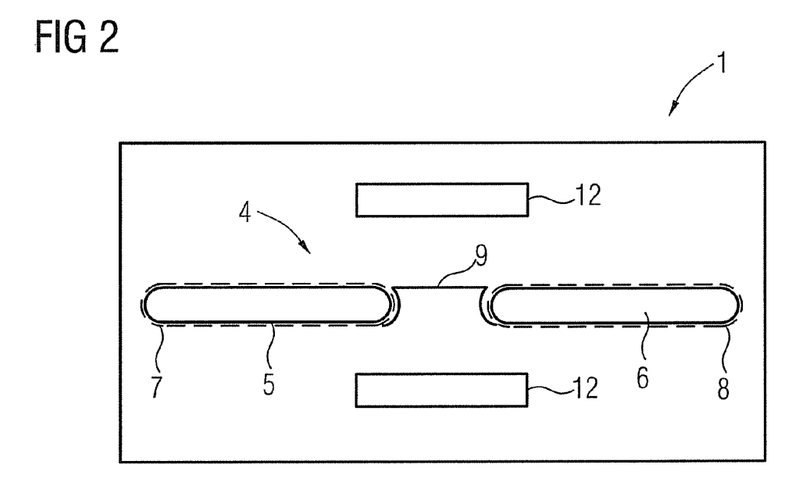
FIG. 2 shows a cross-section through a combined medical examination device with a first embodiment of a patient positioning couch.

FIG. 2 shows a cross-section through the combined medical examination device 1. The PET detector arrangement 12 of the positron emission tomography device 3 is basically of an annular construction and is thus arranged in cross-section above and below the patient positioning couch 4. To explain the basic construction of the patient positioning couch 4 the latter is likewise shown in cross-section. It consists of the plate sections 5 and 6, the respectively assigned conveyor belts 7 and 8, as well as the intermediate element 9. The plate section 6 can be longer than the plate section 5 and to receive the patient it can be moved out of the combined medical examination device 1. The plate section 6 is lowerable outside the examination device 1, which makes it easier to receive the patient. Here the plate section 6 is at least two meters long to be able to receive patients of any size. For special applications, for example special equipment for use in pediatric clinics, it is obviously also possible for the plate section 6 to be shorter. Of course, with a length of at least two meters the combined medical examination device 1 is suitable for practically all patients, it being possible for the ultimate length of the plate section to be specified according to economic standpoints.

The ability of the plate section 6 to be withdrawn and lowered is obviously fulfilled in all example embodiments in which the opening 26 divides the entire cross-section of the patient positioning couch into two large-area plate sections. Accordingly, it is independent of the presence of the intermediate element 9 or of the conveyor belt 7 at the plate section 5.

Figure 3:
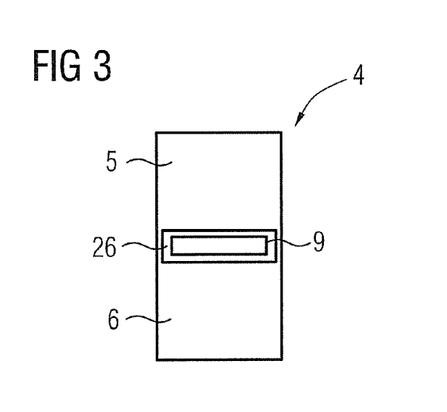
FIG. 3 shows a first embodiment of a patient positioning couch.

FIGS. 3-10 show different embodiments of the patient positioning couch 4. FIG. 3 represents a simple embodiment in which the opening 26 just partially extends over the cross-section of the patient positioning couch 4 and therefore subdivides the patient positioning couch into the two large-area plate sections 5 and 6. Cross struts which permanently interconnect the plate sections 5 and 6 are located at the side of the opening 26. In order to minimize possible radiation attenuation, the elongation of the opening in the longitudinal direction of the patient positioning couch 4 is approximately 20 cm, for example. Accordingly, the width of the opening 26 should be made as wide as possible to avoid any loss of annihilation radiation in the direction of the PET detector arrangement due to the cross struts. The opening 26 can be covered by an intermediate element 9 to prevent sinking, for example of the head of a patient, into the opening 26.

Of course the opening 26 extends over the entire height of the patient positioning couch 4, said opening not being simply a cut-out but also a hole, so to speak. Consequently, apart from the possible intermediate element 9, just air, which, as is known, has an extremely low radiation attenuation coefficient, is located between the area of the patient under examination and the detector elements of the PET detector arrangement 12.

Figure 4:
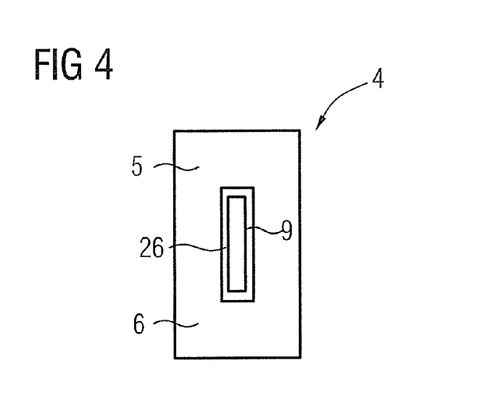
FIG. 4 shows a second embodiment of a patient positioning couch.

FIG. 4 shows a possible adaptation of the patient positioning couch 4 for examinations of the spinal column. For this the opening 26 extends in the longitudinal direction of the patient positioning couch 4, whereby a larger area of the back becomes accessible for examinations by means of the positron emission tomography device 3, which can be recorded without interfering, radiation-attenuating material.

Figure 5:
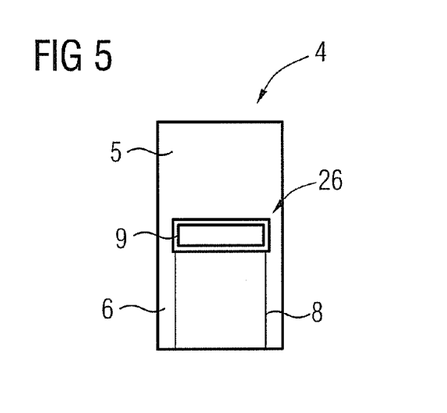
FIG. 5 shows a third embodiment of a patient positioning couch.

FIG. 5 shows a first embodiment of the patient positioning couch which has a conveyor belt 8 at the plate section 6. Otherwise, this embodiment is identical to the embodiment of FIG. 3. The patient can be moved over the opening 26 by way of the conveyor belt 8, which is why the opening no longer has to be elongated for back examinations in the longitudinal direction of the patient positioning couch 4. Rather, the minimum elongation is sufficient for carrying out complete patient examinations in the longitudinal direction. As already described, this length is 20 cm. The patient is moved via the plate section 5 which, if necessary, has an antifriction coating.

Advantageously, at the same time, the width of the conveyor belt 8 is designed so that it fits into the opening 26. Accordingly, the intermediate element 9 is sufficiently spaced away from the plate section 6 so that the conveyor belt 8 can be moved between the intermediate element 9 and the plate section 6.

In this embodiment the intermediate element 9 can be formed as a simple, flat plate which is supported on the cross struts and on the plate section 5. The material should be a type of foam or be porous, and must have sufficient strength to prevent body parts from sinking into it. A minimum radiation attenuation can be realized by the porous construction.

As an alternate to attaching the intermediate element 9 to the cross struts it is also possible to provide the intermediate element 9 with legs on the underside like a chair, which rest next to the PET detector arrangement 12, for example. Since the opening 26 is fixed when a conveyor belt is used, any other attachment to the combined medical examination device 1, which allows movement of the patient along the patient positioning couch 4 is possible.

Figure 6:
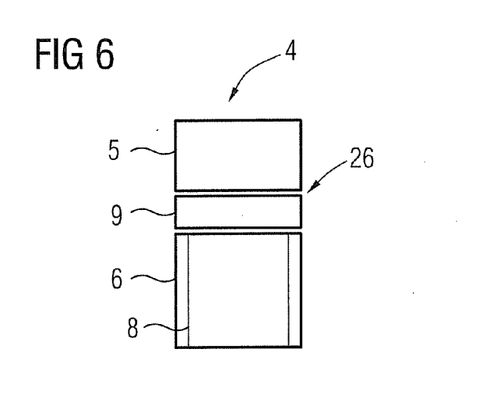
FIG. 6 shows a fourth embodiment of a patient positioning couch.

In the embodiment of FIG. 6, the opening 26 divides the patient positioning couch 4 over the entire cross-section. The opening 26 is covered by way of the intermediate element 9 to prevent body parts sinking into the opening 26. With this arrangement, apart from the intermediate element 9, no components whatsoever are placed between the patient and the PET detector arrangement 12, which facilitates error-free PET measurements. As the intermediate element 9 has to support the patient only over a short distance of 20 cm, it can easily be manufactured from a PET-compatible material such as aramid fiber fabric or foam-type fabric, for example. Accordingly, the intermediate element 9 is invisible, so to speak, to the positron emission tomography device 3.

In contrast to the intermediate element 9, the plate sections 5 and 6 contain a material that does not have to be PET-compatible. Consequently, it is possible to continue to use material used for magnetic resonance devices, without interfering with the operation of additional examination devices, such as the positron emission tomography device 3. Accordingly, research costs for materials which are both magnetic resonance-compatible and PET-compatible, can be avoided or at least minimized. As with the embodiment in FIG. 5, here too only one plate section 6 is provided in the conveyor belt 8.

Figure 7:
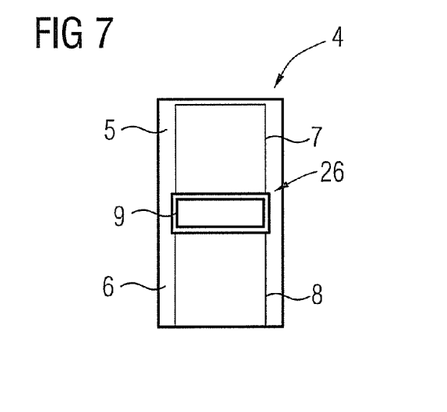
FIG. 7 shows a fifth embodiment of a patient positioning couch.
Figure 8:
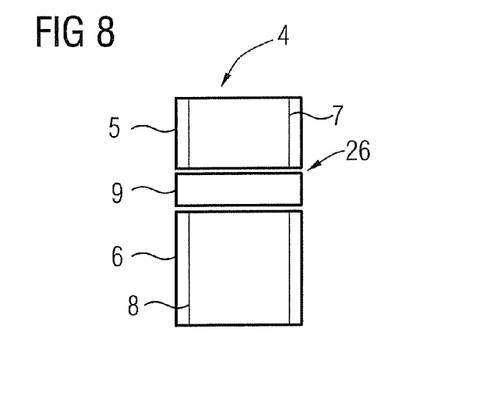
FIG. 8 shows a sixth embodiment of a patient positioning couch.
Figure 9:
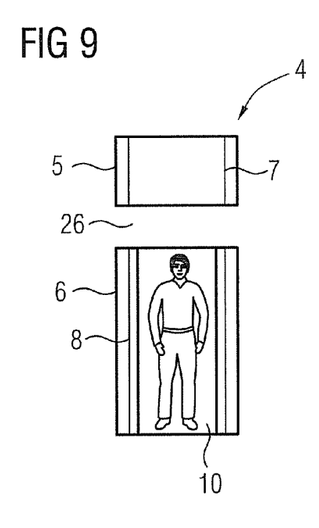
FIG. 9 shows a seventh embodiment of a patient positioning couch.

FIG. 7 shows a patient positioning couch 4 with two conveyor belts 7 and 8. The use of a plurality of conveyor belts or one conveyor belt at each plate section 5, 6 allows the attenuation of the PET radiation as well the frictional forces to be minimized. Friction obviously exists between the patient and the patient positioning couch 4, when moving the patient over the patient positioning couch 4. Where there is only one conveyor belt as partially illustrated in the previous example embodiments, despite the use of friction-minimizing materials on the surface of the patient positioning couch, the problem can arise where, due to friction effects, movement of the patient is not possible. Friction can be minimized due to the presence of one conveyor belt at each plate section. This also applies to the example embodiment of FIG. 8, in which in contrast with FIG. 7 the opening 26 divides the patient positioning couch 4 over the entire cross-section. For further minimization of the friction, the intermediate element 9 can be constructed as a roller. In this case the intermediate element 9 further facilitates the movement of the patient in the longitudinal direction of the patient positioning couch 4.

As already described, the possible sinking of the patient's body parts into the opening 26 is a specific problem. An alternate embodiment to prevent this problem consists in the use of a support element 10. The support element 10 can be used in all embodiments of the patient positioning couch 4 which contain at least one conveyor belt. In this case the patient is fully supported on the support element 10, which appropriately should be approximately 2 m long to receive adult persons. The patient is then moved over the opening 26 on the support element 10—see FIG. 10. Since the center of gravity of the patient is located in the region of the hip, there is no fear of the support element 10 sinking into the opening 26 and blocking the movement. Rather, the patient is supported over the opening 26 in a stable manner.

Figure 10:
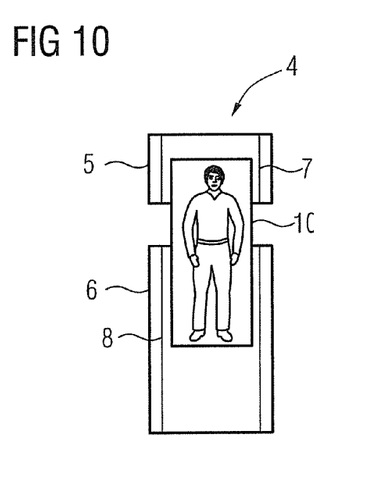
FIG. 10 shows an eighth embodiment of a patient positioning couch.

It should be pointed out at this juncture that in order to facilitate complete full-body examinations, the plate section 5 is obviously smooth so long as the plate section 6 is too. So, during screening of the patient from head to foot, whether he is located on the support element 10 or simply being moved by means of conveyor belts 7 and 8, the patient must be able to be fully supported by the plate section 5.

Figure 11:
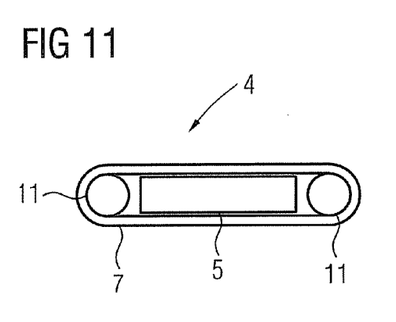
FIG. 11 shows a first embodiment of a plate section.

By way of example, FIG. 11 shows a possible conveyor belt arrangement which can be used with all plate sections. Conveyor rollers 11, by which the conveyor belt 7 is moved, are located at the beginning and end of the plate section 5, it being possible for just one conveyor roller 11 to be driven. For this, textured elements which correlate with textured elements of the conveyor rollers 11 are located on the underside of the conveyor belt 7.

Figure 12:
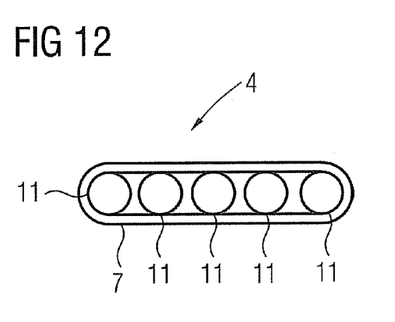
FIG. 12 shows a second embodiment of a plate section.

In a further embodiment a plurality of conveyor rollers 11 is located on the patient positioning couch 4, which consequently forms a plate section. In this embodiment the use of a support element 10 is advantageous in avoiding possible pressure points on the patient during the measurement. Obviously other embodiments for forming the plate sections 5 and 6 are conceivable.

Although only one opening 26 is shown in the embodiments of the patient positioning couch 4, it is obviously possible to provide a plurality of openings 26 in one patient positioning couch 4 and correspondingly also more than two plate sections. Where more than one opening 26 is provided, correspondingly more PET detector arrangements 12 can be used, which allows the measuring time of the positron emission tomography device 3 to be reduced.

Figure 13:
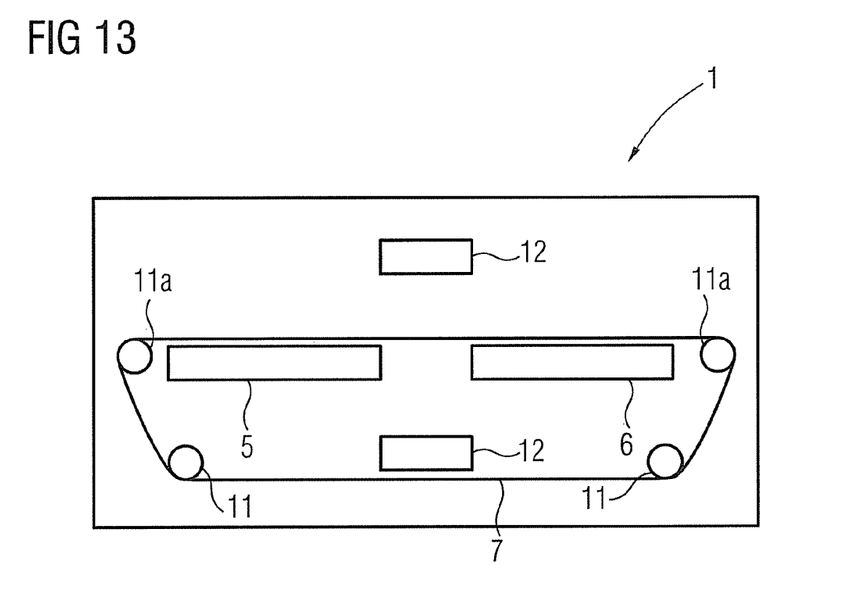
FIG. 13 shows a medical examination device with a ninth embodiment of a patient positioning couch.

FIG. 13 shows a further embodiment of the patient positioning couch 4, in which a single conveyor belt 7 is used for all plate sections 5 and 6. In this arrangement, the conveyor belt 7 can be spaced away from the underside of the support plate, so that only one section of the conveyor belt 7 is located between the PET detector arrangement 12 and a point below the patient. An intermediate element 9 and/or a support element 10 can also be provided in this embodiment to prevent the patient from sinking into the opening 26. The opening 26 can extend just over one partial area or also over the entire cross-section of the patient positioning couch 4. To avoid undesirable radiation attenuation, the conveyor belt 7 is divided into two partial areas. The partial area within the PET detector arrangement 12 for supporting the patient has a smooth underside and also a smooth top side. To enable the conveyor belt to be driven by means of the conveyor rollers 11, only the underside of the conveyor belt 7 has a textured surface in the area of the conveyor rollers 11. In the couch area the conveyor belt is guided via guide rollers 11a.

Figure 14:
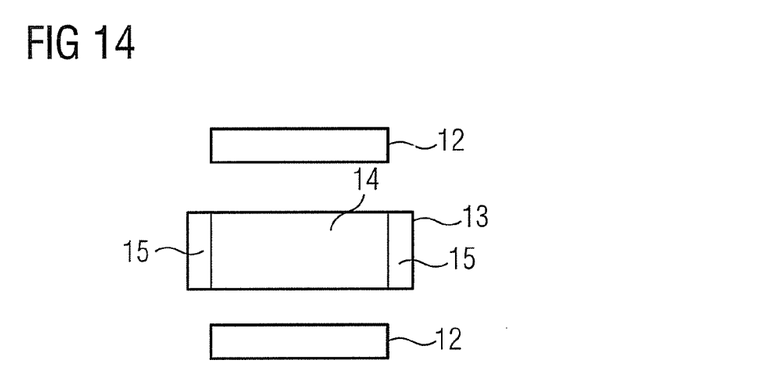
FIG. 14 shows the schematic sketch of a local coil array.

Apart from the patient positioning couch 4, especially in the case of magnetic resonance devices 2, there are further radiation-attenuating devices 2, in particular in the form of the coil arrays 13 normally provided for data recording. The coil array is usually attached to the patient before the start of measurements. In addition, a plurality of partial arrays can be provided, for example a head coil and a plurality of coil arrays on the body. These partial arrays are then moved through the homogeneous region of the magnetic resonance device 2 to obtain sectional image data of the patient's body. The coils 20 of this coil array 13 typically include capacitors, preamplifiers and other radiation-attenuating devices which interfere with the operation of positron emission tomography devices. Accordingly, FIG. 14 shows a combined medical examination device 1, which has a fixed coil array 13. It is thus possible to optimize the coil array for joint use with the PET detector arrangement 12. For this the coil array has a central area 14 and peripheral areas 15, it being possible for the radiation-attenuating components of the coils 20 to be arranged in the peripheral areas 15.

Accordingly, the coil elements which have no or only a slight radiation-attenuating effect are located in the central area 14. With such a type of construction the coil array 13 must of course be able to be dynamically adapted to the object under examination and therefore to different areas of a patient's body. In particular, whole body examinations should obviously be possible with the coil array 13.

Figure 15:
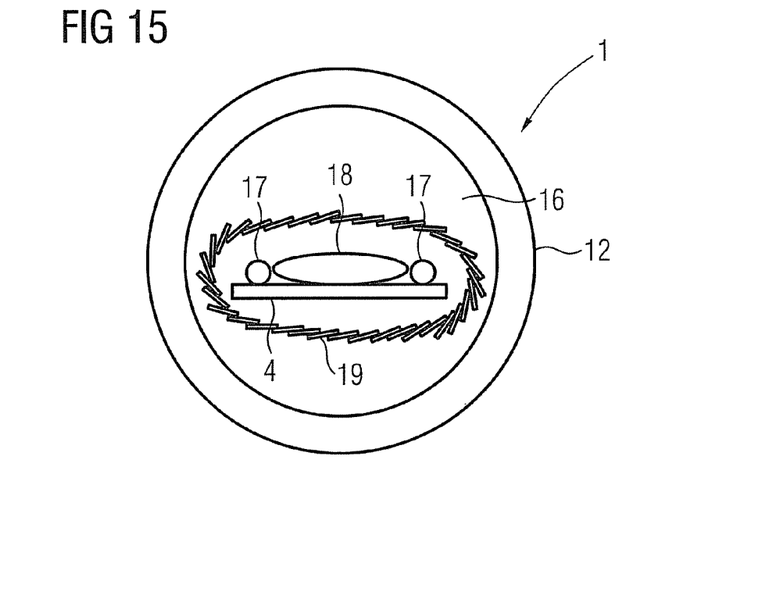
FIG. 15 shows a first embodiment of a combined medical examination device with a local coil array.

FIG. 15 shows a corresponding arrangement, where the line of sight follows inside the bore 16 of the magnetic resonance device 2. The coils of the coil array are arranged on segments 19 of a segmented structure, it being possible for the segments 19 to be moveable against one another. The body of the patient, shown in cross-section by the arms 17 and the body 18, can be covered in this way. At the same time it is therefore easy to swivel the segmented structure inside the cylindrical bore 16.

Figure 16:
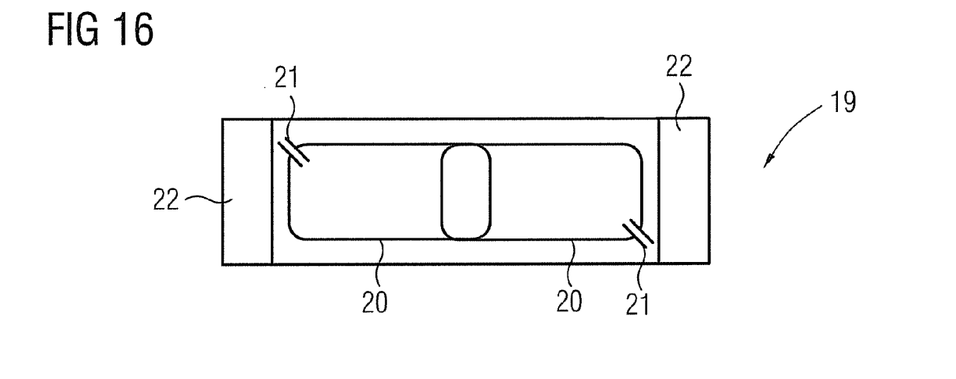
FIG. 16 shows a plan view of a segment of a local coil array.

FIG. 16 shows a plan view of a single segment. The coils 20, which typically include a thin copper layer, are located in the center of the segment. In this case thin means a thickness of approximately 20 μm. In contrast, the radiation-attenuating components such as capacitors 21 or the electronics 22 are located at the peripheral region of the segment 19, which is why the radiation attenuation has been minimized in the central area of the segment 19. During installation, the segment 19 is arranged so that its longitudinal direction coincides with the longitudinal direction of the magnetic resonance device 2.

Figure 17:
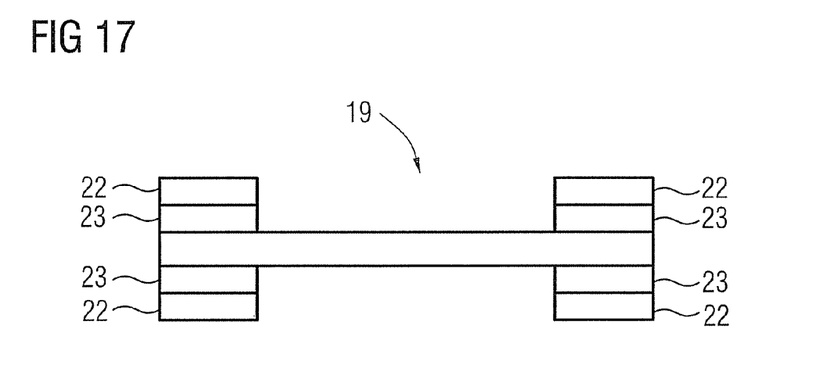
FIG. 17 shows a schematic sketch of a cross-sectional view of a segment of a local coil array.

FIG. 17 shows a cross-sectional view of the segment 19. In addition to the electronics 22, the retainers 23 are also located in the peripheral area of the segment 19. The segments are placed around the patient with the retainers 23.

In order to increase the radiation transmissivity of the segments 19 as far as possible, the support of the segment 19 which houses the coils 20, is formed from foam-type material.

Figure 18:
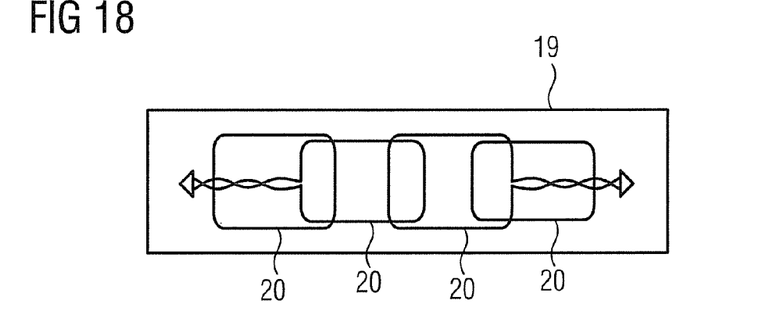
FIG. 18 shows a second embodiment of a segment of a local coil array.

Here the number of coils 20 which can be arranged on one segment 19 is basically optional. Of course each coil 20 needs its own leads, which is why for practical applications a maximum number of four coils 20 can be used, as FIG. 18 shows. In this case, even with four coils 20, leads must be routed in a relatively central area of the segment 19 by which the radiation is attenuated.

Figure 19:
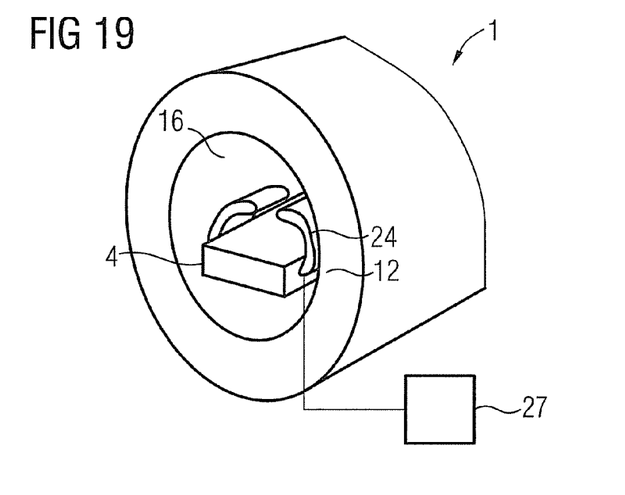
FIG. 19 shows a second embodiment of a combined medical examination device with a local coil array.
Figure 20:
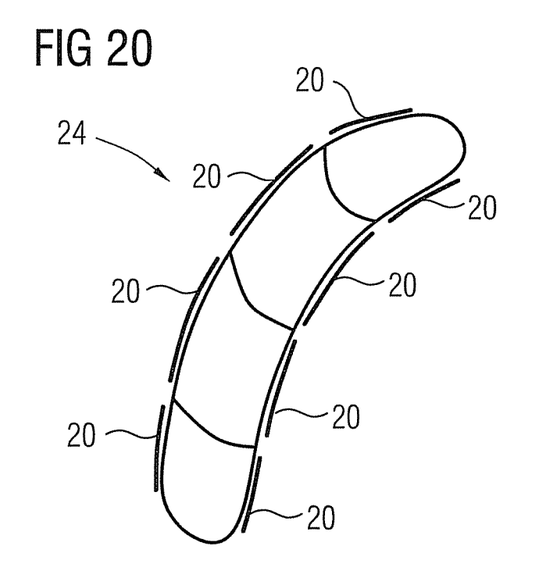
FIG. 20 shows the schematic sketch of a variable-volume device with coils.
Figure 21:
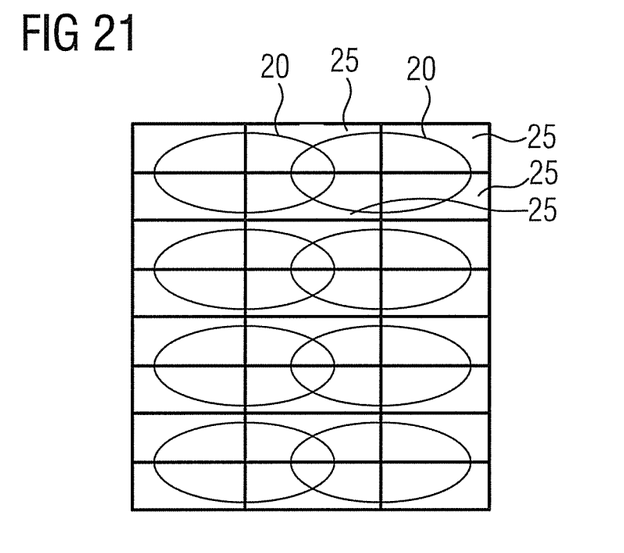
FIG. 21 shows the schematic sketch of a second embodiment of a variable-volume device with coils.

FIG. 19 shows a further possible option for fitting a coil array to a patient. For this the coils 20 are attached to a deformable device 24. The pump 27 is provided for filling the device 24. In order to ensure a definite deformation of the device 24, this is subdivided into chambers 25, as FIG. 20 shows in cross-section. The coils 20 can be assigned to an individual chamber. Alternately, the coils can also overlap each other and/or cover a plurality of chambers 25. FIG. 21 shows a corresponding plan view. For the sake of clarity the coils 20 here are shown oval and the chambers 25 rectangular. The coils 20 can be arranged on the side of the deformable device 24 close to the patient as well as on the side of the deformable device 24 facing away from the patient, it being possible to select either one side or the other. There is no provision for the coils 20 to be mounted simultaneously on both sides.

The device 24 involves a tubular hollow body which can be filled hydraulically or pneumatically with a fluid or gaseous filling medium. In the unfilled state the device 24 is flexible; in the filled and pressurized state the device 24 takes up a predetermined, relatively stiff form. For this, the device 24 consists of a non-elastic plastic material, for example PUR or PTFE, or any other plastic material. The device 24 and each of its chambers has on the side next to the patient a shorter wall section than on the side facing away from the patient, which is why the wall is asymmetrical. When pressurizing the device 24 the individual chambers 25 can be selectively filled, which is why an intentional deformation of the device 24 is possible. During filling, the chambers 25 strive for a smallest possible volume with the smallest surface, and since the wall is non-elastic, a predetermined shape is adopted during filling of the chambers.

The form of the coil arrays 19 with segments as well as with the deformable device 24 can be controlled via sensors which record the dimensions of the patient. The coil array 13 is then matched to the shape of the patient, similar to the way washing devices of a car wash are controlled by way of the external contour of a motor vehicle, for example.

In particular, the use of a fixed coil array enables the receiving electronics and the evaluation electronics assigned to the coil array to be manufactured cost-effectively and simply. Thus, by using a fixed coil array the number of devices in the receiver chain can easily be kept to a minimum. In conventional coil arrays which are moved with the patient, evaluation electronics for driving the coils is required. This can be omitted in the case of a fixed coil array. As a result, on the one hand the construction in relation to the use of further imaging-type examination devices is improved and on the other hand it is also cost-effective to realize.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention.

Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE NUMBERS

1 Combined medical examination device
2 Magnetic resonance device
3 Positron emission tomography device
4 Patient positioning couch
5 Plate section
6 Conveyor belt
7 Conveyor belt
8 Intermediate element
9 Support element
10 Conveyor roller
11a Guide roller
11 PET detector arrangement
12 Coil array
13 Central region
14 Peripheral region
15 Body coil
16 Arm
17 Body
18 Segment
19 Coil
20 Capacitor
21 Electronics
22 Retainer
23 Deformable device
24 Chamber
25 Opening
26 Pump

What is claimed is:

1. A patient positioning couch compatible with a combined medical examination device, comprising:
a support plate having a top surface and a bottom surface, the top surface configured to support a patient positioned thereon, the support plate including at least one opening penetrating the top surface and the bottom surface;
an intermediate element provided on a portion of the top surface, the intermediate element configured to support a portion of the patient positioned on the support plate over the at least one opening by at least partially covering the at least one opening; and
at least one conveyor belt to move the patient on the support plate in a longitudinal direction, wherein
the at least one opening divides the support plate into two large-area plate sections in a partial area of a cross-section.

2. The patient positioning couch as claimed in claim 1, wherein at least one of the two separate large-area plate sections is at least one of lowerable, moveable in the longitudinal direction of the patient positioning couch, and partially shaped obliquely to the horizontal.

3. The patient positioning couch as claimed in claim 1, wherein at least one of the two separate large-area plate sections is longer in the horizontal direction than at least a second one of the two separate large-area plate sections.

4. The patient positioning couch as claimed in claim 1, wherein the at least one conveyor belt includes at least two conveyor belts and wherein each of the two plate sections includes a corresponding one of the conveyor belts.

5. The patient positioning couch as claimed in claim 1, wherein the at least one conveyor belt includes a single conveyor belt and wherein the two plate sections share the single conveyor belt.

6. The patient positioning couch as claimed in claim 5, wherein a part of the shared conveyor belt, that runs under the support plate, is spaced away from the support plate so that a space is created between the support plate and the shared conveyor belt to house items.

7. The patient positioning couch as claimed in claim 5, wherein the shared conveyor belt includes two belt sections, a first of the two sections, which is used to receive the patient, including a smooth underside and the second of the two sections including a textured underside.

8. The patient positioning couch as claimed in claim 5, wherein the shared conveyor belt consists of aramid fiber fabric.

9. A combined medical examination device, comprising:
at least two imaging arrangements; and
a patient positioning couch compatible with the combined medical examination device, the patient positioning couch including,
a support plate having a top surface and a bottom surface, the top surface configured to support a patient positioned thereon, the support surface including at least one opening penetrating the top surface and the bottom surface,
an intermediate element provided on a portion of the top surface, the intermediate element configured to support a patient positioned on the support plate over the at least one opening by at least partially covering the at least one opening, and
at least one conveyor belt to move the patient on the support plate in a longitudinal direction, wherein the at least one opening divides the support plate into two large-area plate sections in a partial area of a cross-section.

10. The combined medical examination device as claimed in claim 9, wherein a first of the at least two imaging arrangements includes an X-ray device or a computer tomography device or a magnetic resonance device.

11. The combined medical examination device as claimed in claim 9, wherein a second of the at least two imaging arrangements includes a positron emission tomography device or a scintigraphy device.

12. The combined medical examination device as claimed in claim 10, wherein the first of the at least two imaging arrangements is a magnetic resonance device including a fixed coil array in the longitudinal direction of the magnetic resonance device.

13. The combined medical examination device as claimed in claim 12, wherein the coil array at least one of includes a variable diameter and is hingeable.

14. The combined medical examination device as claimed in claim 13, wherein, in order to arrange the coil array on the patient, at least one section of the coils of the coil array is attached to a device whose volume can be varied hydraulically or pneumatically.

15. The combined medical examination device as claimed in claim 13, wherein, in order to arrange the coil array on the patient, at least one section of the coils of the coil array is arranged so as to be moveable together on a segmented structure.

16. The combined medical examination device as claimed in claim 12, wherein the coil array is formed in a central region in relation to the longitudinal axis, with less radiation attenuation than in the peripheral regions.

17. A patient positioning couch compatible with a combined medical examination device, comprising:
a support plate having a top surface and a bottom surface, the top surface configured to support a patient positioned thereon, the support plate including at least one opening penetrating the top surface and the bottom surface;
an intermediate element provided on a portion of the top surface, the intermediate element configured to support a portion of the patient positioned on the support plate over the at least one opening by at least partially covering the at least one opening; and
at least one conveyor belt to move the patient on the support plate in a longitudinal direction wherein
the at least one opening divides the support plate into two separate large-area plate sections over an entire cross-section,
at least one of the two separate large-area plate sections is at least one of lowerable, moveable in the longitudinal direction of the patient positioning couch, and partially shaped obliquely to the horizontal, and
at least one of the two separate large-area plate sections is longer in the horizontal direction than at least a second one of the two separate large-area plate sections.

18. The combined medical examination device as claimed in claim 10, wherein a second of the at least two imaging arrangements includes a positron emission tomography device or a scintigraphy device.

19. The combined medical examination device as claimed in claim 10, wherein a second of the at least two imaging arrangements includes a positron emission tomography device or a scintigraphy device.

20. A patient positioning couch for a combined medical examination device, comprising:
a support plate having a top surface and a bottom surface, the top surface configured to support a patient positioned thereon, the support plate including at least one opening penetrating the top surface and the bottom surface and positioned over a cross section of the support plate to at least partially divide the support plate into two plate sections having the at least one opening therebetween; and
a single conveyor belt configured to move the patient on the support plate by rotating around the two plate sections having the at least one opening therebetween such that a side of the single conveyer belt is separated from the at least one opening by a distance to house an imaging arrangement therebetween.

* * * * *